United States Patent [19]

Decker et al.

[11] 4,339,355

[45] Jul. 13, 1982

[54] CATALYTIC OXIDE OF MOLYBDENUM, VANADIUM, NIOBIUM AND OPTIONAL 4TH METAL

[75] Inventors: Harry J. Decker; Erlind M. Thorsteinson, both of Charleston, W. Va.

[73] Assignee: Union Carbide Corporation, Danbury, Conn.

[21] Appl. No.: 841,056

[22] Filed: Oct. 11, 1977

Related U.S. Application Data

[60] Division of Ser. No. 621,088, Oct. 9, 1975, abandoned, which is a continuation-in-part of Ser. No. 505,780, Sep. 13, 1974, abandoned, which is a continuation-in-part of Ser. No. 408,419, Oct. 23, 1973, abandoned.

[51] Int. Cl.$^3$ .................. B01J 23/22; B01J 23/26; B01J 23/28; B01J 23/34
[52] U.S. Cl. ........................... 252/464; 252/467; 562/534; 562/535

[58] Field of Search .............. 252/455 R, 456, 464, 252/467, 470; 260/530 N

[56] References Cited

U.S. PATENT DOCUMENTS

| | | | |
|---|---|---|---|
| 3,875,220 | 4/1975 | White et al. ................... | 252/467 X |
| 3,926,915 | 12/1975 | Watanabe et al. ............. | 260/530 N |
| 3,936,505 | 2/1976 | Oda et al. ........................ | 568/477 |
| 4,014,927 | 3/1977 | Kadowaki ........................ | 562/534 |
| 4,035,262 | 7/1977 | Childress et al. ............... | 252/456 |

*Primary Examiner*—W. J. Shine
*Attorney, Agent, or Firm*—Bernard Francis Crowe

[57] ABSTRACT

A novel catalyst comprising the elements Mo, V and Nb is provided for oxidizing alpha-beta unsaturated aliphatic aldehydes in the vapor phase with molecular oxygen to produce the corresponding alpha-beta unsaturated carboxylic acid.

5 Claims, No Drawings

CATALYTIC OXIDE OF MOLYBDENUM, VANADIUM, NIOBIUM AND OPTIONAL 4TH METAL

CROSS-REFERENCE TO RELATED PATENT APPLICATION

This patent application is a division of application Ser. No. 621,088 filed Oct. 9, 1975 which was a continuation-in-part of application Ser. No. 505,780 filed Sept. 13, 1974 which was a continuation-in-part of application Ser. No. 408,419 filed Oct. 23, 1973, all now abandoned.

BACKGROUND OF THE INVENTION

1. Field of the Invention

The invention relates to the vapor phase catalytic oxidation of unsaturated aliphatic aldehydes to the corresponding unsaturated aliphatic carboxylic acid.

2. Description of the Prior Art

The use of molybdenum and vanadium containing catalyst systems for the gas phase oxidation of alpha-beta unsaturated aliphatic aldehydes, such as acrolein, to the corresponding alpha-beta-unsaturated carboxylic acids, such as acrylic acid, has been known.

In these reactions a gaseous reaction mixture which usually contains the aldehyde, molecular oxygen and water, as steam, is brought into contact with the catalyst, by continuously passing a stream of the reaction mixture through a bed of the catalyst. Such known catalyst systems would include those disclosed in the following U.S. Pat. Nos. 3,087,964; 3,358,020; 3,408,392; 3,435,069; 3,439,028; 3,530,175; 3,567,772; 3,567,773; 3,574,729; 3,644,509; 3,655,749; 3,670,017 and 3,703,548. Not all of these catalyst systems, however, are currently useful for commercial purposes. Some of these catalyst systems, for example, do not provide the relatively high levels of % conversion, productivity and % selectivity, which are all required, presently, of a commercially useful catalyst system.

The terms % conversion, productivity, and % selectivity which are employed herein with respect to the present invention are defined as follows:

$$\% \text{ conversion} = 100 \times \frac{A}{\text{moles of aldehyde in the reaction mixture which is fed to the catalyst bed}} \quad \text{I}$$

wherein $A$ = the molar aldehyde-equivalent sum (carbon basis) of all carbon-containing products, excluding the aldehyde in the effluent  Ia $$\text{productivity} = \text{pounds of alpha-beta unsaturated aliphatic carboxylic acid product produced per cubic foot of catalyst (in the catalyst bed) per hour of reaction time} \quad \text{II}$$

$$\% \text{ selectivity (or efficiency)} = 100 \times \frac{\text{moles of alpha-beta-unsaturated aliphatic carboxylic acid produced}}{A} \quad \text{III}$$

wherein A is defined above in equation Ia.

SUMMARY OF THE INVENTION

Alpha-beta-unsaturated aliphatic carboxylic acids are produced with a relatively high % conversion, productivity and % selectivity by oxidizing the corresponding alpha-beta-unsaturated aldehyde in the vapor phase by contacting the aldehyde, in the presence of molecular oxygen and steam, with certain catalyst compositions containing molybdenum, vanadium and niobium.

An object of the present invention is to provide novel catalyst compositions for the vapor phase oxidation of alpha-beta-unsaturated aliphatic aldehydes to the corresponding alpha-beta-unsaturated aliphatic carboxylic acid.

A further object of the present invention is to provide a process whereby alpha-beta-unsaturated aliphatic aldehydes can be oxidized in the gas phase so as to produce the corresponding alpha-beta-unsaturated aliphatic carboxylic acid with a relatively high level of % conversion, productivity and % selectivity.

These and other objects of the present invention are achieved by using as such a catalyst in such a process a composition comprising the elements Mo, V, Nb and X in the ratio $$Mo_a V_b Nb_c X_d$$

wherein X is Co, Cr, Cu, Fe, In, Mn and/or Y,
a is 12,
b is 0.1 to 20, and preferably 1 to 14, and most preferably 2 to 8,
c is 0.1 to 12, and preferably 0.5 to 2, and
d is 0 to 3.0, and preferably 0.01 to 1.0.

The numerical values of a, b, c and d represent the relative gram-atom ratios of the elements Mo, V, Nb, and X, respectively, which are present in the catalyst composition.

THE CATALYST

The elements Mo, V, Nb, and X are present in the catalyst composition in combination with oxygen in the form, it is believed, of various metal oxides, as such, and possibly as chemical combinations of oxides such as spinels and perovskites.

The catalyst is preferably prepared from a solution of soluble salts and/or complexes and/or compounds of each of the metals Mo, V, Nb and X. The solution is preferably an aqueous system having a pH of 1-12, and preferably 5±3, at a temperature of about 20° to 100° C. The solution of the metal containing compounds is prepared by dissolving sufficient quantities of soluble compounds of each of the metals, so as to provide the desired a:b:c:d atom-mole ratios of the elements Mo, V, Nb and X, respectively. The selected salts, complexes or compounds of the metals Mo, V, and Nb should be mutually soluble. If the selected salts, complexes or compounds of the metal X are not mutually soluble with the other metal compounds, they can be added last to the solution system. The catalyst composition is then prepared by removing the water or other solvent from the mixture of the metal compounds in the solution system. Any portion, and preferably i.e. about <50 weight %, of the niobium may be replaced by titanium and/or tantalum in the catalyst composition.

The water or other solvent can be removed from the mixture of the dissolved metal compounds by evaporation.

The catalyst may be used on an inert support which may be silica, alumina or silica-alumina. Where the catalyst is to be used on a support, the metal compounds are deposited on a porous support usually having a surface area of about 0.01 to 500, and preferably 0.1 to 2, square meters per gram. The support has an apparent porosity of 30–60%; at least 90% of the pores have a pore diameter in the range of 20–1500 microns. The support is usually used in the form of particles or pellets which are about ⅛ to 5/16 inch in diameter. The deposition is accomplished by immersing the support in the solution and then evaporating off the major portion of the solvent, and then drying the system at about 80° to 140° C. for 2 to 60 hours. The dried catalyst is then calcined by being heated at 200° to 550° C., and preferably 325°–425° C., for 2 to 24 hours in air to produce the desired $Mo_aV_bNb_cX_d$ composition.

When used on the support, the supported oxides usually comprise about 10 to 50 weight % of the total catalyst composition, with the remainder being the support.

The molybdenum is preferably introduced into solution in the form of ammonium salts thereof such as ammonium paramolybdate, and organic acid salts of molybdenum such as acetates, oxalates, mandelates and glycolates. Other water soluble molybdenum compounds which may be used are partially water soluble molybdenum oxides, molybdic acid, and the nitrates and chlorides of molybdenum.

The vanadium is preferably introduced into solution in the form of ammonium salts thereof such as ammonium meta-vanadate and ammonium decavanadate, and organic acid salts of vanadium such as acetates, oxalates and tartrates. Other water soluble vanadium compounds which may be used are partially water soluble vanadium oxides, and the sulfates and nitrates of vanadium.

The niobium is preferably introduced into solution in the form of oxalates. Other sources of soluble niobium which may be used are niobium compounds in which the niobium is coordinated, bonded, or complexed to a beta-diketonate, a carboxylic acid, an amine, an alcohol or an alkanolamine.

Where titanium is used for a portion of the niobium, the titanium is preferably introduced into solution in the form of a water soluble chelate coordinated with ammonium lactate. Other soluble titanium compounds which may be used are those in which titanium is coordinated, bonded, or complexed to a beta-diketonate, a carboxylic acid, an amine, an alcohol or an alkanolamine.

Where tantalum is used for a portion of the niobium, the tantalum is preferably introduced into solution in the form of oxalates. Other sources of soluble tantalum which may be used are tantalum compounds in which the tantalum is coordinated, bonded, or complexed to a beta-diketonate, a carboxylic acid, an amine, an alcohol or an alkanolamine.

The cobalt, chromium, copper, iron, indium, manganese and yttrium are preferably introduced into solution in the form of nitrates. Other water soluble compounds of these elements which may be used are the water soluble chlorides and organic acid salts such as the acetates, oxalates, tartrates, lactates, salicylates, formates and carbonates of such metals.

It is believed that, for the catalysts to be most effective, the Mo, V, Nb, X metal components should be slightly reduced below their highest possible oxidation states. This may be accomplished during the thermal treatment of the catalyst in the presence of reducing agents such as $NH_3$ or organic reducing agents, such as the organic complexing agents, which are introduced into the solution systems from which the catalysts are prepared. The catalyst may also be reduced in the reactors in which the oxidation reaction is to be conducted by the passage of hydrogen or hydrocarbon reducing agents such as ethane, ethylene or propylene through the catalyst bed.

THE ALDEHYDES

The alpha-beta-unsaturated aldehydes which are oxidized in the process of the present invention have the structure

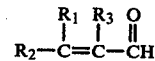

wherein $R_1$ is H or a $C_1$–$C_6$ alkyl radicals and $R_2$ and $R_3$ are the same or different and are H or $CH_3$.

These aldehydes thus include acrolein and methacrolein. Where acrolein and/or methacrolein are oxidized, the corresponding alpha-beta-unsaturated carboxylic acid would be acrylic acid and/or methacrylic acid, respectively.

The aldehydes may be oxidized individually or in combinations thereof.

THE REACTION MIXTURE

The components of the reaction mixtures which are employed in the process of the present invention, and the relative ratios of the components in such mixtures, are the following 1 mole of aldehyde, 0.2 to 5 moles of molecular oxygen (as pure oxygen or in the form of air), 1 to 25 moles of water (in the form of steam), and optionally, 0.1 to 5 moles of alpha-beta-unsaturated olefin having the same number of carbon atoms as the aldehyde being oxidized. Propylene, for example, can be used in the reaction mixture when acrolein is being oxidized to acrylic acid.

The water, or steam, can be used as a reaction diluent and as a heat moderator for the reaction. Other diluents which may be used are inert gases such as nitrogen, $CO_2$ and gaseous saturated hydrocarbons.

The olefin may be present due to the fact that the aldehyde feed may be emanating as the effluent from an olefin→aldehyde oxidation reaction process, and such effluent usually contains unreacted olefin.

The components of the reaction mixture are uniformly admixed prior to being introduced into the reaction zone. The components are preheated, individually or after being admixed, prior to their being introduced into the reaction zone, to a temperature of about 200° to 300° C.

REACTION CONDITIONS

The preheated reaction mixture is brought into contact with the catalyst composition, in the reaction zone, under the following conditions:

pressure of about 1 to 10, and preferably of about 1 to 3 atmospheres, temperature of about 200° to 400° C., and preferably of about 250° to 350° C., contact time (reaction mixture on catalyst) of about 0.1 to 10, and preferably of about 1 to 3, seconds, and a space velocity of about 1000 to 6000 $h^{-1}$, preferably 4000 to 5000 $h^{-1}$.

The contact time may also be defined as the ratio between the apparent volume of the catalyst bed and the volume of the gaseous reaction mixture fed to the catalyst bed under the given reaction conditions in a unit of time.

The reaction pressure is initially provided by the feed of gaseous reactants and diluents, and after the reaction is commenced, the pressure is maintained, preferably, by the use of suitable back-pressure controllers placed on the gaseous effluent side of the catalyst bed.

The reaction temperature is preferably provided by placing the catalyst bed within a tubular converter whose walls are immersed in a suitable heat transfer medium, such as tetralin, molten salt mixtures, or other suitable heat transfer agent, which is heated to the desired reaction temperature.

The following examples are merely illustrative of the present invention and are not intended as a limitation upon the scope thereof.

The examples provided below disclose the preparation of various catalyst compositions, and the use of such compositions in the oxidation of acrolein to acrylic acid.

The activity of each experimental catalyst was determined in a jacketed one-inch stainless steel reactor or converter tube 78 inches long. The jacket contained tetralin which served as a heat transfer medium.

The center portion (55 inches) of the reactor tube was charged with 800 ml of catalyst with a one-eighth inch movable thermocouple in the catalyst bed.

The catalysts were tested at 30 psig, with a space velocity of 4600 $hr^{-1}$ or contact time of 1.2 seconds, and an inlet feed composed of 3 mole % acrolein, 6 mole % oxygen, 15 mole % steam, and 75 mole % nitrogen.

The activity of the catalysts was tested by adjusting the temperature of the reactor tube jacket to produce a maximum temperature (hot spot) of 304°–306° C. in the catalyst bed, while the oxidation reaction was occurring.

Space velocity is calculated by determining the total reactor outlet gas equivalents (liters) of the total effluent evolved over a period of one hour. This room temperature volume is converted to the volume at 0° C. at 760 mm Hg.

$$\text{Space Velocity} = \frac{\text{liters of outlet gas equivalents/hour}}{\text{liters of catalyst in reactor}} \quad \text{IV}$$

$$= \frac{1}{\text{hours at 0° C. and atmospheric pressure}} = h^{-1}$$

EXAMPLE 1

$Mo_{2.4}V_{0.6}Nb_{0.3}Co_{0.15}$ or $Mo_{12}V_3Nb_{1.5}Co_{0.75}$

Seventy grams of ammonium meta-vanadate (0.6 gram atoms of V) and 424 grams of ammonium paramolybdate (2.4 gram atoms of Mo) were dissolved in two liters of water while stirring at 60°–80° C. in a stainless steel beaker.

To the resulting solution were added 475 grams of niobium oxalate solution (containing 0.3 gram atoms Nb) and 36 grams of copper nitrate [$Cu(NO_3)_2 \cdot 3H_2O$] (0.15 gram atoms Cu) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 27.5 weight percent. Catalytic test results for this material are given in Table I.

EXAMPLE 2

$Mo_{2.4}V_{0.6}Nb_{0.3}Fe_{0.15}$ or $Mo_{12}V_3Nb_{1.5}Fe_{0.75}$

Seventy grams of ammonium meta-vanadate (0.6 gram atoms of V) and 424 grams of ammonium paramolybdate (2.4 gram atoms of Mo) were dissolved in two liters of water while stirring at 60°–80° C. in a stainless steel beaker.

To the resulting solution were added 474 grams of niobium oxalate solution (95.3 gms $Nb_2O_5$/l) (0.3 gram atoms Nb) and 60 grams of ferric nitrate [$Fe(NO_3)_3 \cdot 9H_2O$] (0.15 gram atoms Fe) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 24.4 weight percent. Catalytic test results for this material are given in Table I.

EXAMPLE 3

$Mo_{2.4}V_{0.6}Nb_{0.3}Mn_{0.15}$ or $Mo_{12}V_3Nb_{1.5}Mn_{0.75}$

Seventy grams of ammonium meta-vanadate (0.6 gram atoms of V) and 424 grams of ammonium paramolybdate (2.4 grams atoms of Mo) were dissolved in two liters of water while stirring at 60°–80° C. in a stainless steel beaker.

To the resulting solution were added 475 grams of niobium oxalate solution (95.3 gms. $Nb_2O_5$/l) (0.3 gram atoms Nb) and 54 grams of 50.3% manganous nitrate aqueous solution (0.15 gram atoms Mn).

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 27.5 weight %. Catalytic test results of this material are given in Table I.

EXAMPLE 4

$Mo_{2.4}V_{0.6}Fe_{0.15}$ or $Mo_{12}V_3Fe_{0.75}$

Seventy grams of ammonium meta-vanadate (0.6 gram atoms of V) and 424 grams of ammonium paramolybdate (2.4 grams of Mo) were dissolved in two liters of water while stirring at 60°–80° C. in a stainless steel beaker.

To the resulting solution were added 60 grams ferric nitrate $[Fe(NO_3)_3.9H_2O]$ (0.15 gram atoms Fe) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 27.5 weight percent. Catalytic test results for this material are given in Table I.

EXAMPLE 5

$Mo_{2.4}V_{0.6}Fe_{0.15}$ (made with 0.75 (mole) parts $(NH_4)_2$ oxalate) or $Mo_{12}V_3Fe_{0.75}$ Seventy grams of ammonium meta-vanadate (0.6 gram atoms of V) and 424 grams of ammonium paramolybdate (2.4 gram atoms of Mo) were dissolved in two liters of water while stirring at 60°–80° C. in a stainless steel beaker.

To the resulting solution were added 107 grams of ammonium oxalate $[(NH_4)_2C_2O_4.H_2O]$ (0.75 gram moles $(NH_4)_2C_2O_4$) and 60 grams of ferric nitrate $[Fe(NO_3)_3.9H_2O]$ (0.15 gram atoms Fe) dissolved in 100-ml water.

The resulting mixture was heated while stirring and approximately 60 percent of the water was evaporated off.

The resulting mixture was heated while stirring and approximately 60 percent of the water was evaporated off.

The resulting concentrated slurry was transferred to a stainless steel evaporating dish and 1040 grams (1000 ml) Norton silica-alumina (#SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 26.3 weight percent. Catalytic test results for this material are given in Table I.

EXAMPLE 6

$Mo_{2.8}V_{0.7}$ or $Mo_{12}V_3$

Eighty-two grams of ammonium meta-vanadate (0.7 gram atoms of V and 256 grams of oxalic acid (2.1 moles) were dissolved in two liters of water while stirring at 60°–80° C. in a stainless steel beaker.

To the resulting solution were added 495 grams of ammonium paramolybdate (2.8 gram atoms Mo) dissolved in 1 l. water.

The resulting mixture was heated while stirring and approximately 60 percent of the water was evaporated off.

The resulting concentrated slurry was transferred to a stainless steel evaporating dish and 1040 grams (1000 ml) Norton silica-alumina (#SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 26.5 weight %. Catalytic test results for this material are given in Table I.

EXAMPLE 7

$Mo_{2.4}V_{0.6}Cu_{0.15}$ or $Mo_{12}V_3Cu_{0.75}$

Seventy grams of ammonium meta-vanadate (0.6 gram atoms of V) and 424 grams of ammonium paramolybdate (2.4 gram atoms of Mo) were dissolved in two liters of water while stirring at 60°–80° C. in a stainless steel beaker.

To the resulting solution were added 90 grams of ammonium lactate solution (containing 0.6 gram mole $NH_4$ lactate) and 36 grams of copper nitrate $[Cu(NO_3)_2.3H_2O]$ (0.15 gram atoms Cu) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° C. in an ambient atmosphere of air. The amount of catalyst deposited on the support calculated from the weight increase of the catalyst obtained is 26.0 weight %. Catalytic test results for this material are given in Table I below.

EXAMPLE 8

$Mo_{2.8}V_{0.7}Nb_{0.35}$ or $Mo_{12}V_3Nb_{1.5}$

Eighty-two grams of ammonium meta-vanadate (0.7 gram atoms of V) and 494 grams of ammonium paramolybdate (2.8 gram atoms of Mo) were dissolved in two liters of water while stirring at 60°–80°, in a stainless steel beaker.

To the resulting solution were added 550 grams of niobium oxalate solution (containing 0.35 gram atoms Nb) and 28 grams of ammonium nitrate (0.35 gram moles NH$_4$NO$_3$) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. 5218) ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 27.7%. Catalytic test results for this material are given in Table II below.

EXAMPLE 9

Mo$_{2.4}$V$_{0.6}$Nb$_{0.3}$ or Mo$_{12}$V$_3$Nb$_{1.5}$

Seventy grams of ammonium meta-vanadate (0.6 gram atoms of V) and 424 grams of ammonium paramolybdate (2.4 gram atoms of Mo) were dissolved in two liters of water while stirring at 60°–80°, in a stainless steel beaker.

To the resulting solution there was added a slurry of 40 grams of niobium pentoxide (containing 0.3 gram atoms of Nb) in 300 ml of a solution containing 0.6 moles of ammonium lactate and 0.3 moles of ammonium nitrate. The ammonium lactate was formed from 55 grams of lactic acid (in 100 ml of H$_2$O) and 37 grams of NH$_4$OH (29 weight % NH$_4$OH in 100 ml H$_2$O). The ammonium nitrate (29 grams in 100 ml of H$_2$O) was added to equalize the nitrate content of this system, prior to drying, with the nitrate content of catalyst systems containing the X element(s). The Nb$_2$O$_5$ did not dissolve.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. 5218) ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 27.6%. Catalytic test results for this material are given in Table II below.

EXAMPLE 10

Mo$_{2.4}$V$_{0.6}$Nb$_{0.3}$Cr$_{0.15}$ or Mo$_{12}$V$_3$Nb$_{1.5}$Cr$_{0.75}$

Seventy grams of ammonium meta-vanadate (0.6 gram atoms of V) and 424 grams of ammonium paramolybdate (2.4 gram atoms of Mo) were dissolved in two liters of water while stirring at 60°–80°, in a stainless steel beaker.

To the resulting solution were added 280 grams of niobium oxalate solution (containing 0.3 gram atoms Nb) and 60 grams of chromium nitrate enneahydrate (0.15 gram atoms Cr) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. 5218) ¼″ spheres were added. This was followed by drying by evaporation with stirring on a steam bath. Further drying was carried out at a temperature 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 23.1%. Catalytic test results for this material are given in Table II below.

EXAMPLE 11

Mo$_{2.4}$V$_{0.6}$Nb$_{0.3}$Co$_{0.15}$ or Mo$_{12}$V$_3$Nb$_{1.5}$Co$_{0.75}$

Seventy grams of ammonium meta-vanadate (0.6 gram atoms of V) and 424 grams of ammonium paramolybdate (2.4 gram atoms of Mo) were dissolved in two liters of water while stirring at 60°–80°, in a stainless steel beaker.

To the resulting solution were added 475 grams of niobium oxalate solution (containing 0.3 gram atoms Nb) and 44 grams of cobalt nitrate hexahydrate (0.15 gram atoms Co) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. 5218) ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 27.5%. Catalytic test results for this material were given in Table II below.

EXAMPLE 12

Mo$_{2.4}$P$_{0.6}$Nb$_{0.3}$ or Mo$_{12}$P$_3$Nb$_{1.5}$

Sixty eight grams of 86.1% phosphoric acid in 200 ml H$_2$O (0.6 gram atoms of P) and 424 grams of ammonium paramolybdate (2.4 gram atoms of Mo) were dissolved in two liters of water while stirring at 60°–80°, in a stainless steel beaker.

To the resulting solution were added 273 grams of niobium oxalate solution containing 0.3 gram atoms Nb dissolved in 300-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. 5218) ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 17.5%. The catalytic results for this material are given in Table III below.

EXAMPLE 13

$Mo_{2.4}P_{0.6}Nb_{0.3}Cu_{0.15}$ or $Mo_{12}P_3Nb_{1.5}Cu_{0.75}$

Sixty eight grams of 86.1% phosphoric acid in 200 ml $H_2O$ (0.6 gram atoms of P) and 35.2 grams of ammonium hydroxide in 100 ml $H_2O$ (0.6 gram atoms of N) and 424 grams of ammonium paramolybdate (2.4 gram atoms of Mo) were dissolved in two liters of water while stirring at 60°–80°, in a stainless steel beaker.

To the resulting solution were added 273 grams of niobium oxalate solution (containing 0.3 gram atoms Nb) dissolved in 300 ml of $H_2O$ and 36 grams of cupric nitrate (0.15 gram atoms Cu) dissolved in 100-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. 5218) ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 20.9%. The catalytic results for this material are given in Table III below.

The support used in Examples 1–13 was essentially an (~86/14) $Al_2O_3/SiO_2$ material having an apparent porosity of 36–42% and a surface area of $<1$ m²/gram. About 100% of the pores in the support had a pore diameter of about 20–180 microns.

The pH of the solutions used in each of Examples 1–13 for the preparation of the catalysts was in the range of $5\pm3$.

The results of Examples 1 to 3 (reported below in Table I) Examples 8, 10 and 11 (reported in Table II) demonstrate that when the catalyst compositions are prepared in accordance with the teachings of the present invention, as described above, the resulting catalysts provide a combination of relatively high levels of % conversion, productivity and % selectivity in the oxidation of alpha-beta unsaturated aldehydes such as acrolein to the corresponding alpha-beta unsaturated acid.

The results of Examples 4 to 7 reported below in Tables I and II demonstrate that not all compositions containing the elements Mo, V and X, as defined above, provide catalysts which can be used in the oxidation of alpha-beta unsaturated aldehydes such as acrolein to produce the corresponding alpha-beta unsaturated acid at relatively high levels of % conversion, productivity and % selectivity.

The results of Example 9 demonstrate the desirability of providing the elements in the form of soluble compounds and complexes. The niobium was used in the form of water-insoluble $Nb_2O_5$ and the resulting catalyst provided poor results.

The results of Examples 12 and 13, as reported in Table III below, in comparison to the results of Examples 8 and 1, respectively, demonstrate that the use of phosphorous, in lieu of vanadium in the catalysts of the present invention, does not produce acceptable results.

TABLE I

| Example | Catalyst Description Atomic Ratios | Metal* Oxides in Catalyst % | Hot Spot °C. | Conversion % | AA/Ft³ Cat. /hr. Lbs. | Efficiency % |
|---|---|---|---|---|---|---|
| 1 | $Mo_{2.4}V_{0.6}Nb_{0.3}Cu_{0.15}$ | 27.5 | 301 | 91.8 | 24.40 | 92.9 |
| 2 | $Mo_{2.4}V_{0.6}Nb_{0.3}Fe_{0.15}$ | 24.4 | 306 | 87.3 | 22.50 | 93.6 |
| 3 | $Mo_{2.4}V_{0.6}Nb_{0.3}Mn_{0.15}$ | 27.5 | 295 | 94.5 | 23.80 | 92.4 |
| 4 | $Mo_{2.4}V_{0.6}Fe_{0.15}$ | 27.5 | 305 | 13.4 | 2.20 | 58.0 |
| 5 | $Mo_{2.4}V_{0.6}Fe_{0.15}$[a] | 26.3 | 318 | 20.3 | 3.10 | 50.9 |
| 6 | $Mo_{2.8}V_{0.7}$[b] | 26.5 | 305 | 7.7 | 1.40 | 62.9 |
| 7 | $Mo_{2.4}V_{0.6}Cu_{0.15}$[c] | 26.0 | 305 | 30.4 | 7.40 | 83.9 |

AA = acrylic acid
[a] Used 0.75 (mole) parts ammonium oxalate.
[b] Used 2.1 (mole) parts oxalic acid.
[c] Used 0.60 (mole) parts ammonium lactate.
*oxides of the metals Mo, V, Nb, and/or X.

calcined in a muffle furnace for 5 hours at 400° in an

TABLE II

| Example | Catalyst Description Atomic Ratios | Metal* Oxides in Catalyst % | Hot Spot °C. | Conversion % | AA/Ft³ Cat. /hr. Lbs. | Efficiency % |
|---|---|---|---|---|---|---|
| 4 | $Mo_{2.4}V_{0.6}Fe_{0.15}$ | 27.5 | 305 | 13.4 | 2.20 | 58.0 |
| 5 | $Mo_{2.4}V_{0.6}Fe_{0.15}$[a] | 26.3 | 318 | 20.3 | 3.10 | 50.9 |
| 6 | $Mo_{2.8}V_{0.7}$[b] | 26.5 | 305 | 7.7 | 1.40 | 62.9 |
| 7 | $Mo_{2.4}V_{0.6}Cu_{0.15}$[c] | 26.0 | 305 | 30.4 | 7.40 | 83.9 |
| 8 | $Mo_{2.8}V_{0.7}Nb_{0.35}$[d] | 27.7 | 295 | 92.2 | 24.5 | 91.5 |
| 9 | $Mo_{2.4}V_{0.6}Nb_{0.3}$[e] | 27.6 | 305 | 29.4 | 6.3 | 78.0 |
| 10 | $Mo_{2.4}V_{0.6}Nb_{0.3}Cr_{0.15}$ | 23.1 | 304 | 86.2 | 21.6 | 93.0 |

TABLE II-continued

| Example | Catalyst Description Atomic Ratios | Metal* Oxides in Catalyst % | Hot Spot °C. | Conversion % | AA/Ft³ Cat. /hr. Lbs. | Efficiency % |
|---|---|---|---|---|---|---|
| 11 | $Mo_{2.4}V_{0.6}Nb_{0.3}Co_{0.15}$ | 27.5 | 305 | 96.9 | 23.9 | 90.0 |

AA = acrylic acid
(a) Used 0.75 (mole) parts ammonium oxalate.
(b) Used 2.1 (mole) parts oxalic acid.
(c) Used 0.60 (mole) parts ammonium lactate.
(d) Used 0.35 (mole) parts ammonium nitrate.
(e) Used 0.3 gram atoms $Nb_2O_5$ and 0.6 moles ammonium lactate.
*oxides of the metals Mo, V, Nb, and/or X.

TABLE III

| Example | Catalyst Description Atomic Ratios | Metal** Oxides in Catalyst, % | Hot Spot °C. | Conversion % | AA/Ft³ Cat /hr., lbs. | Efficiency % |
|---|---|---|---|---|---|---|
| 8 | $Mo_{2.8}V_{0.7}Nb_{0.35}$ (d) | 27.7 | 295 | 92.2 | 24.5 | 91.5 |
| 1 | $Mo_{2.4}V_{0.6}Nb_{0.3}Cu_{0.15}$ | 27.5 | 301 | 91.8 | 24.40 | 92.9 |
| 12 | $Mo_{2.4}P_{0.6}Nb_{0.3}$ | 17.5 | 305 | 28.65 | 5.6 | 72.50 |
| 13 | $Mo_{2.4}P_{0.6}Nb_{0.3}Cu_{0.15}$ | 20.9 | 304 | 5.85 | 1.1 | 67.23 |

AA = acrylic acid.
**Oxides of the metals Mo, B, Nb, P and/or X.
(d) Used 0.35 (mole) parts ammonium nitrate.

EXAMPLES 14–25

Catalysts 14–25 were prepared as disclosed below, and evaluated in the experimental catalyst test procedure described above. Each of the catalysts of Examples 14–25 contain the elements Mo, V and Nb in various ratios, and, in addition, the catalysts of Examples 14, 16, 23, 24 and 25 also contain at least one of the X elements. The composition of each of these catalysts is given at the heading of the respective examples, and the test results are reported in Table IV below.

The supports used in Examples 24–25 was the same as that used in Examples 1–13. The support used in Examples 14, 15, and 17–23 was an ($\sim$86/14) $Al_2O_3/SiO_2$ material having an apparent porosity of $\sim$52% and a surface area of <1 m²/gram. About 90% of the pores in this support had a pore diameter of about 50–400 microns.

The support used in Example 16 was predominantly alumina. It contained only 0.35% Si. This support had an apparent porosity of about 62% and a surface area of <1 m²/gram. About 90% of the pores in this support had a pore diameter of about 2–100 microns.

The pH of the solutions used in each of Examples 14–25 for the preparation of the catalysts was in the range of 5±3.

The results of Examples 14–25 demonstrate the relatively high levels of % conversion, % efficiency and productivity that can be obtained with the catalysts of the present invention for the oxidation of alpha-beta unsaturated aliphatic aldehydes such as acrolein to the corresponding alpha-beta unsaturated carboxylic acid.

EXAMPLE 14

$Mo_{12}V_3Nb_{1.5}Cu_{0.75}$ or $Mo_{1.08}V_{0.27}Nb_{0.135}Cu_{0.0675}$

32 Grams of ammonium meta-vanadate (0.27 gram atoms of V) and 191 grams of ammonium paramolybdate (1.08 gram atoms of Mo) were dissolved in two liters of water while stirring at 60°–80°, in a stainless steel beaker.

To the resulting solution were added 124 grams of niobium oxalate solution containing 0.135 gram atoms Nb plus 17 grams of copper nitrate [$Cu(NO_3)_2\cdot 3H_2O$] (0.0675 gram atoms Cu) dissolved in 100-ml water.

The resulting mixture was heated while stirring and approximately 60 percent of the water was evaporated off.

The resulting concentrated slurry was transferred to a stainless steel evaporating dish and 770 grams (1000 ml) Norton silica-alumina (No. SA-5205) ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 20.3%.

EXAMPLE 15

$Mo_{12}V_{1.5}Nb_{0.75}$ or $Mo_{2.64}V_{0.33}Nb_{0.165}$ 38.6 Grams of ammonium meta-vanadate (0.33 gram atoms of V) and 466 grams of ammonium paramolybdate (2.64 gram atoms of Mo) were dissolved in two liters of water while stirring at 60°–80°, in a stainless steel beaker.

To the resulting solution were added 260 grams of niobium oxalate solution containing 0.165 gram atoms Nb.

The resulting mixture was heated while stirring and approximately 60 percent of the water was evaporated off.

The resulting concentrated slurry was transferred to a stainless steel evaporating dish and 770 grams (1000 ml) Norton silica-alumina (No. SA-5205) ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 27.8%.

EXAMPLE 16

$Mo_{12}V_3Nb_{1.5}Cu_{0.75}$ or $Mo_{1.32}V_{0.33}Nb_{0.166}Cu_{0.0825}$ 39.0 Grams of ammonium meta-vanadate (0.33 gram atoms of V) and 233 grams of ammonium paramolybdate (1.32 gram atoms of Mo) were dissolved in two liters of water while stirring at 60°–80°, in a stainless steel beaker.

To the resulting solution were added 260 grams of niobium oxalate solution containing 0.166 gram atoms Nb plus 20 grams of copper nitrate [$Cu(NO_3)_2.3H_2O$] containing 0.75 gram atoms Cu dissolved in 100 ml water.

The resulting mixture was heated while stirring and approximately 60 percent of the water was evaporated off.

The resulting concentrated slurry was transferred to a stainless steel evaporating dish and 687 grams(1000 ml) Norton alumina (No. 5513) 5/16″ rings were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 17.4%.

EXAMPLE 17

$Mo_{12}V_6Nb_3$ or $Mo_{1.32}V_{0.66}Nb_{0.33}$

77 Grams of ammonium meta-vanadate (0.66 grams atoms of V) and 233 grams of ammonium paramolybdate (1.32 gram atoms of Mo) were dissolved in two liters of water while stirring at 60°–80°, in a stainless steel beaker.

To the resulting solution were added 519 grams of niobium oxalate solution containing 0.33 gram atoms Nb.

The resulting mixture was heated while stirring and approximately 60 percent of the water was evaporated off.

The resulting concentrated slurry was transferred to a stainless steel evaporating dish and 770 grams (1000 ml) Norton silica-alumina (No. 5205) ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 4.4%.

EXAMPLE 18

$Mo_{12}V_6Nb_{1.5}$ or $Mo_{1.2}V_{0.6}Nb_{0.15}$

70 Grams of ammonium meta-vanadate (0.6 gram atoms of V) and 212 grams of ammonium paramolybdate (1.2 gram atoms of Mo) were dissolved in two liters of water while stirring at 60°–80°, in a stainless steel beaker.

To the resulting solution were added 236 grams of niobium oxalate solution containing 0.15 gram atoms Nb.

The resulting mixture was heated while stirring and approximately 60 percent of the water was evaporated off.

The resulting concentrated slurry was transferred to a stainless steel evaporating dish and 770 grams (1000 ml) Norton silica-alumina (No. SA-5205) ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air.

The amount of catalyst deposited on the support calculated from the weight increase of the catalyst obtained is 20.5%.

EXAMPLE 19

$Mo_{12}V_{12}Nb_{1.5}$ or $Mo_{1.1}V_{1.1}Nb_{0.138}$

129 Grams of ammonium meta-vanadate (1.1 gram atoms of V) and 194 grams of ammonium paramolybdate (1.1 gram atoms of Mo) were dissolved in two liters of water while stirring at 60°–80°, in a stainless steel beaker.

To the resulting solution were added 216 grams of niobium oxalate solution containing 0.138 gram atoms Nb.

The resulting mixture was heated while stirring and approximately 60 percent of the water was evaporated off.

The resulting concentrated slurry was transferred to a stainless steel evaporating dish and 770 grams (1000 ml) Norton silica-alumina (No. SA-5205) ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air.

The amount of catalyst deposited on the support calculated from the weight increase of the catalyst obtained is 20.4%.

EXAMPLE 20

$Mo_{12}V_{0.75}Nb_{1.5}$ or $Mo_{1.6}V_{0.1}Nb_{0.2}$

Twelve grams of ammonium meta-vanadate (0.1 gram atoms of V) and 283 grams of ammonium paramolybdate (1.6 gram atoms of Mo) were dissolved in two liters of water while stirring at 60°–80°, in a stainless steel beaker.

To the resulting solution were added 315 grams of niobium oxalate solution containing 0.2 gram atoms Nb.

The resulting mixture was heated while stirring and approximately 60 percent of the water was evaporated off.

The resulting concentrated slurry was transferred to a stainless steel evaporating dish and 770 grams (1000 ml) Norton silica-alumina (No. SA-5205) ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air.

The amount of catalyst deposited on the support calculated from the weight increase of the catalyst obtained is 17.3%.

EXAMPLE 21

$Mo_{12}V_{0.375}Nb_{1.5}$ or $Mo_{1.7}V_{0.053}Nb_{0.213}$ 6.23 Grams of ammonium meta-vanadate (0.053 gram atoms of V) and 300 grams of ammonium paramolybdate (1.7 gram atoms of Mo) were dissolved in two liters of water while stirring at 60°-80°, in a stainless steel beaker.

To the resulting solution were added 335 grams of niobium oxalate solution containing 0.213 gram atoms Nb.

The resulting mixture was heated while stirring and approximately 60 percent of the water was evaporated off.

The resulting concentrated slurry was transferred to a stainless steel evaporating dish and 770 grams (1000 ml) Norton silica-alumina (No. SA-5205) ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 15.2%.

EXAMPLE 22

$Mo_{12}V_{18}Nb_{1.5}$ or $Mo_{0.9}V_{1.35}Nb_{0.113}$

158 Grams of ammonium meta-vanadate (1.35 gram atoms of V) and 159 grams of ammonium paramolybdate (0.9 gram atoms of Mo) were dissolved in two liters of water while stirring at 60°-80°, in a stainless steel beaker.

To the resulting solution were added 177 grams of niobium oxalate solution containing 0.113 grams atoms Nb.

The resulting mixture was heated while stirring and approximately 60 percent of the water was evaporated off.

The resulting concentrated slurry was transferred to a stainless steel evaporating dish and 770 grams (1000 ml) Norton silica-alumina (No. SA-5205) ¼″ spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 22.1%.

EXAMPLE 23

$Mo_{2.4}V_{0.6}Nb_{0.3}Fe_{0.03}Cu_{0.03}Co_{0.03}Cr_{0.03}Mn_{0.03}$ or $Mo_{12}V_3Nb_{1.5}Fe_{0.15}Cu_{0.15}Co_{0.15}Cr_{0.15}Mn_{0.15}$

70 Grams of ammonium meta-vanadate (0.6 gram atoms of V) and 424 grams of ammonium paramolybdate (2.4 gram atoms of Mo) were dissolved in two liters of water while stirring at 60°-80°, in a stainless steel beaker.

To the resulting solution was added 472 grams of niobium oxalate solution containing 0.3 gram atoms Nb plus 12.2 grams of $Fe(NO_3)_3.9H_2O$ (0.03 grams-atoms Fe) plus 7.25 grams $Cu(NO_3)_2.3H_2O$ (0.03 grams-atoms Cu) plus 8.73 grams $Co(NO_3)_2.6H_2O$ (0.03 gram atoms Co) plus 12.0 grams $Cr(NO_3)_3.9H_2O$ (0.03 gram atoms Cr) plus 10.67 grams of 50.3% $Mn(NO_3)_2$ solution (0.03 gram atoms Mn) dissolved in 129 ml water.

The resulting mixture was heated while stirring and approximately 60 percent of the water was evaporated off.

The resulting concentrated slurry was transferred to a stainless steel evaporating dish and 770 grams (1000 ml) Norton silica-alumina (No. SA-5205) ¼″ spheres were added. This was followed by drying of evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 27.2%.

EXAMPLE 24

$Mo_{12}V_3Nb_{1.5}Y_{0.75}$ or $Mo_{1.92}V_{0.48}Nb_{0.24}Y_{0.12}$

56 Grams of ammonium meta-vanadate (0.48 gram atoms of V) and 339 grams of ammonium paramolybdate (1.92 gram atoms of Mo) were dissolved in two liters of water while stirring at 60°-80°, in a stainless steel beaker.

To the resulting solution were added 218 grams of niobium oxalate solution containing (0.24 gram atoms Nb) plus 44 grams of yttrium nitrate $[Y(NO_3)_3.5H_2O]$ (0.12 gram atoms Y) dissolved in 80-ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼″ spheres were added. This was followed by drying by evaporation with stirring on a steam bath. Further drying was carried out at a temperature of 120° C. for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 13.0%.

EXAMPLE 25

$Mo_{12}V_3Nb_{1.5}In_{0.75}$ or $Mo_{1.92}V_{0.48}Nb_{0.24}In_{0.12}$

56 Grams of ammonium meta-vanadate (0.48 gram atoms of V) and 339 grams of ammonium paramolybdate (1.92 gram atoms of Mo) were dissolved in two liters of water while stirring at 60°-80°, in a stainless steel beaker.

To the resulting solution were added 218 grams of niobium oxalate solution containing (0.24 gram atoms Nb) plus 47 grams of indium nitrate [In(NO$_3$)$_3$.5H$_2$O] (0.12 gram atoms In) dissolved in 80 ml water.

The resulting mixture was heated while stirring and approximately 60 percent of the water was evaporated off.

The resulting concentrated slurry was transferred to a stainless steel evaporating dish and 1040 grams (1000 ml) Norton silica-alumina (No. SA-5218) ¼" spheres were added. This was followed by drying by evaporation with stirring on a steam bath. Further drying was carried out at a temperature of 120° for a period of 16 hours.

The dried material was then transferred to a tray fabricated from 10-mesh stainless steel wire screen and calcined in a muffle furnace for 5 hours at 400° in an ambient atmosphere of air. The amount of catalyst deposited on the support calculated from the weight increase of the catalyst obtained is 12.2%.

elements Mo, V, Nb and X, respectively, which are present in such catalyst composition.

On a relative atom-mole ratio basis, therefore, the catalysts of the present invention encompass those in which a is 15,
b is 0.125 to 25 and preferably 1.25 to 17.5, and most preferably 2.5 to 10,
c is 0.125 to 15, and preferably 1.25 to 2.5, and
d is 0 to 3.75, and preferably 0.0125 to 1.25.

What is claimed is:

1. An oxidation catalyst containing the elements Mo, V, Nb and X, in the form of oxides, in the ratio $$Mo_aV_bNb_cX_d$$

wherein X is at least one element selected from the group consisting of Cr, Cu, Mn and Y,

TABLE IV

| Example No. | Catalyst Description Atomic Ratios | Metal* Oxides in Catalyst % | Hot Spot, °C. | Conversion % | A.A./ Cu.Ft. of Catalyst /hr., lbs. | Efficiency % |
|---|---|---|---|---|---|---|
| 14 | Mo$_{1.08}$V$_{0.27}$Nb$_{0.135}$Cu$_{0.0675}$ | 20.3 | 304 | 98.3 | 25.0 | 94.5 |
| 15 | Mo$_{2.64}$V$_{0.33}$Nb$_{0.165}$ | 27.8 | 305 | 96.8 | 24.3 | 90.9 |
| 16 | Mo$_{1.32}$V$_{0.33}$Nb$_{0.166}$Cu$_{0.083}$ | 17.4 | 305 | 75.4 | 20.8 | 94.6 |
| 17 | Mo$_{1.32}$V$_{0.66}$Nb$_{0.33}$ | 4.4 | 305 | 57.7 | 15.0 | 92.3 |
| 18 | Mo$_{1.2}$V$_{0.6}$Nb$_{0.15}$ | 20.5 | 303 | 91.6 | 24.8 | 91.0 |
| 19 | Mo$_{1.1}$V$_{1.1}$Nb$_{0.138}$ | 20.4 | 304 | 96.2 | 21.9 | 88.4 |
| 20 | Mo$_{1.6}$V$_{0.1}$Nb$_{0.2}$ | 17.3 | 304 | 95.0 | 24.8 | 92.7 |
| 21 | Mo$_{1.7}$V$_{0.053}$Nb$_{0.213}$ | 15.2 | 305 | 86.6 | 21.7 | 90.9 |
| 22 | Mo$_{0.9}$V$_{1.35}$Nb$_{0.113}$ | 22.1 | 304 | 87.2 | 18.0 | 76.8 |
| 23 | Mo$_{2.4}$V$_{0.6}$Nb$_{0.3}$Fe$_{0.03}$Cu$_{0.03}$Co$_{0.03}$Cr$_{0.03}$ Mn$_{0.03}$ | 27.2 | 305 | 97.6 | 24.8 | 92.6 |
| 24 | Mo$_{1.92}$V$_{0.48}$Nb$_{0.24}$Y$_{0.12}$ | 13.0 | 305 | 78.3 | 19.0 | 93.9 |
| 25 | Mo$_{1.92}$V$_{0.48}$Nb$_{0.24}$In$_{0.12}$ | 12.2 | 305 | 78.4 | 19.9 | 94.6 |

*Oxides of the metals Mo, V, Nb and X.

As noted above the catalyst of the present invention comprises the elements Mo, V, Nb and X in the ratio $$Mo_aV_bNb_cX_d$$

wherein X is Co, Cr, Cu, Fe, In, Mn and/or Y,
a is 12,
b is 0.1 to 20, and preferably 1 to 14, and most preferably 2 to 8,
c is 0.1 to 12 and preferably 0.5 to 2, and
d is 0 to 3.0 and preferably 0.01 to 1.0.

It is also noted above that the numerical values of a, b, c and d represent the relative atom-mole ratios of the a is 12,
b is 0.1 to 20,
c is 0.1 to 12, and
d is 0 to 3.0 said catalyst being devoid of catalytically active forms of tellurium, phosphorus and oxides of silicon.

2. A catalyst as in claim 1 in which X comprises Cr.
3. A catalyst as in claim 1 in which X comprises Cu.
4. A catalyst as in claim 1 in which X comprises Mn.
5. A catalyst as in claim 1 in which X comprises Y.

* * * * *